(12) United States Patent
Nolte et al.

(10) Patent No.: US 8,725,850 B2
(45) Date of Patent: May 13, 2014

(54) AUTOMATIC CONNECTIVITY ANALYSIS FOR A DICOM NETWORK

(75) Inventors: Björn Nolte, Fürth (DE); Thomas Sebille, Erlangen (DE); Angelika Siclaru, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 39 days.

(21) Appl. No.: 13/291,128

(22) Filed: Nov. 8, 2011

(65) Prior Publication Data

US 2012/0117205 A1 May 10, 2012

(30) Foreign Application Priority Data

Nov. 10, 2010 (DE) .......................... 10 2010 043 718

(51) Int. Cl.
*G06F 15/16* (2006.01)
(52) U.S. Cl.
USPC ........................................................ 709/220
(58) Field of Classification Search
None
See application file for complete search history.

(56) References Cited

U.S. PATENT DOCUMENTS

| | | | | |
|---|---|---|---|---|
| 5,046,063 | A * | 9/1991 | LaGess | 370/282 |
| 6,494,831 | B1 * | 12/2002 | Koritzinsky | 600/301 |
| 2002/0103514 | A1 * | 8/2002 | Abrahamson | 607/60 |
| 2007/0118635 | A1 * | 5/2007 | Nakano | 709/223 |
| 2008/0208046 | A1 * | 8/2008 | Pierce | 600/437 |
| 2010/0138523 | A1 * | 6/2010 | Urness et al. | 709/222 |
| 2010/0205485 | A1 | 8/2010 | Sakaue et al. | |
| 2011/0145373 | A1 * | 6/2011 | Awad et al. | 709/220 |

OTHER PUBLICATIONS

German priority application DE 10 2010 043 718.2 filed on Nov. 10, 2010 (not yet published).

* cited by examiner

*Primary Examiner* — Jason K. Gee
*Assistant Examiner* — Christopher C Harris
(74) *Attorney, Agent, or Firm* — Harness, Dickey & Pierce, P.L.C.

(57) ABSTRACT

A method, a computer program product, a system and a connectivity analyzer are disclosed for determining available communication functionalities during the configuration of a DICOM node in a DICOM network. According to an embodiment of the invention the available communication functionalities are registered automatically by way of test communication requests and analysis of the test communication responses. Following the analysis the result containing the detected communication functionalities can be provided automatically. The result is preferably provided in the configuration phase and already prior to the entry into operation of the respective DICOM node.

9 Claims, 2 Drawing Sheets

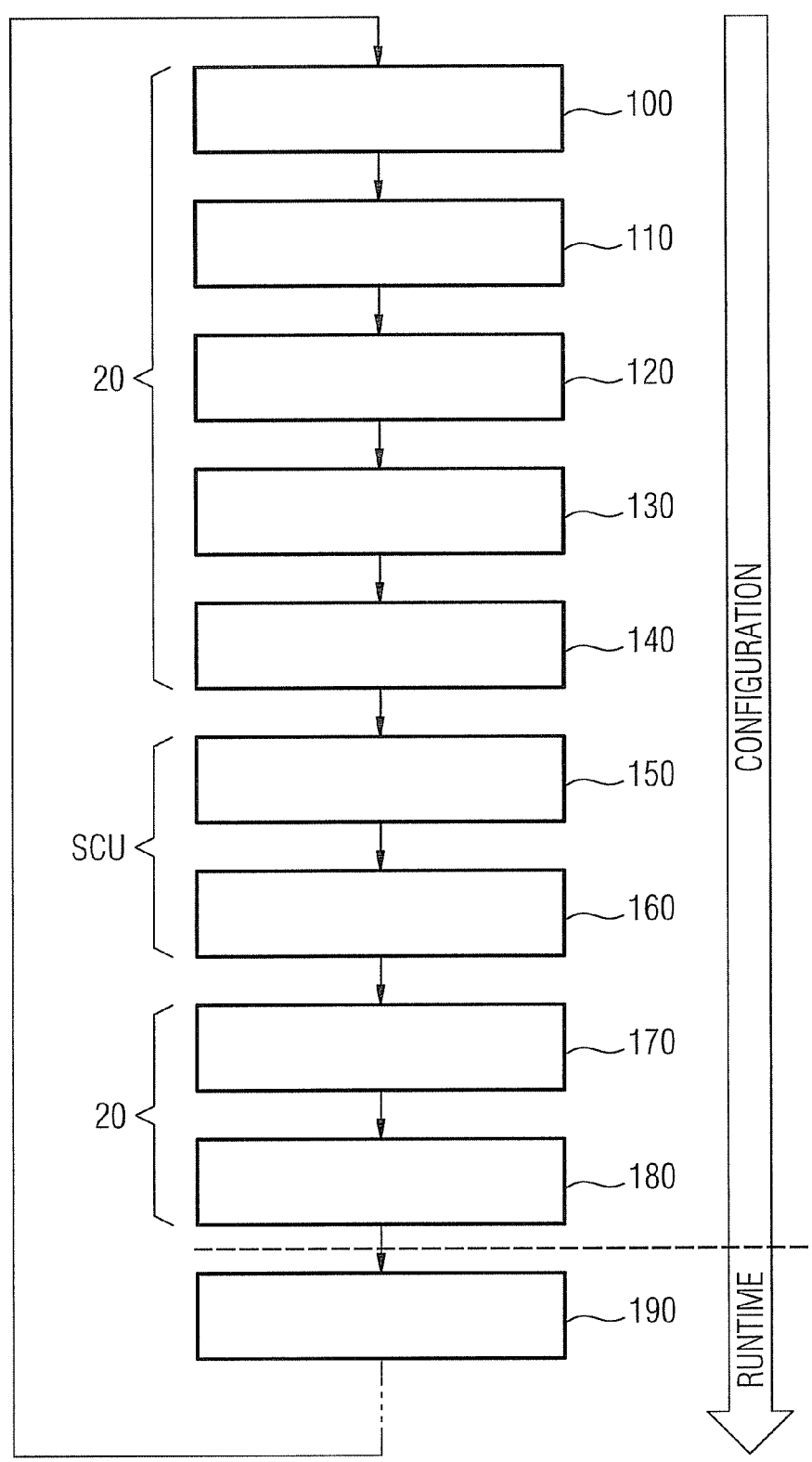

AUTOMATIC CONNECTIVITY ANALYSIS FOR A DICOM NETWORK

PRIORITY STATEMENT

The present application hereby claims priority under 35 U.S.C. §119 on German patent application number DE 10 2010 043 718.2 filed Nov. 10, 2010, the entire contents of which are hereby incorporated herein by reference.

FIELD

At least one embodiment of the present invention lies in the fields of information technology and medical engineering and generally relates to an approach for determining available communication functionalities during the configuration of DICOM devices in a DICOM network.

BACKGROUND

The digitization of imaging medicine has resulted in a multiplicity of different digital terminal devices from different manufacturers being employed today in contemporary radiological image processing systems. Moreover these devices are required to exchange data with one another. The DICOM standard, currently acknowledged as the most important standard in radiology, was developed back in 1993 in order to enable these devices to interact in a standardized manner. The DICOM standard is patterned after the ISO-OSI reference model and supports communication in heterogeneous systems. At the same time the DICOM standard also guarantees the exchange of data (this is referred to as connectivity). However, the DICOM standard has no influence on the applications which use the data that is to be transmitted. Essentially, a terminal device can process and use the data only if it is possible also to transfer the data to the device. This is referred to as interoperability. A prerequisite for interoperability therefore is that all the devices connected to the network (or DICOM nodes) are capable of exchanging data.

Owing to the multiplicity of devices requiring to be deployed (for example MR scanners, post-processing systems, monitors, antennas for transmitting the signals of the MR device, etc.) and due to the fact that the terminal devices come from different manufacturers that develop the respective devices and on account of the different communication functionalities of the devices, provision is made to provide in advance at a preliminary stage what is referred to as a declaration of conformity (conformance statement). The conformance statement is usually drafted by the manufacturer and serves to specify which DICOM functions (in particular which DICOM services and options) are supported by the respective device.

It has hitherto proved disadvantageous in the prior art that the conformance statements are only completed in a rudimentary manner and in some cases are provided in such an unsatisfactory manner that no connectivity analysis is possible. If a new DICOM network is to be built or an existing one modified or extended, a (new) DICOM device must be integrated into the DICOM network. Depending on its function this DICOM device engages in data interchange with other DICOM devices. To enable this data interchange to be performed without error, it is necessary to verify in advance whether the respective devices are interoperable. This situation can be explained in a simplified exemplary manner with reference to the following example: If an MR scanner is to forward its acquired data to a post-processing module, it is necessary to verify as a preliminary step whether the post-processing module can actually receive the data provided by the MR scanner in the respective format and, for example, whether the data communication envisaged between the two devices has sufficient capacity. In order to be able to prevent an error due to defective connectivity between the participating DICOM nodes in the actual application case, a connectivity analysis must be carried out at a preliminary stage. Disadvantageously, this has not been possible in the past due to the inadequacy of the conformance statements provided.

SUMMARY

In at least one embodiment of the invention, an analytical tool is provided, which all the essential DICOM communication parameters are analyzed and presented automatically. In particular, in at least one embodiment it is aimed to be possible to analyze the connectivity between different DICOM terminal devices of different manufacturers at a preliminary stage and in advance of an actual connection setup in order to be able to establish connectivity wherever possible at the preliminary stage by reconciling connection parameters.

At least one embodiment is directed to a method, a computer program product, a system and/or a connectivity analyzer.

An embodiment of the invention is described in more detail below with reference to the method by way of example. Alternative embodiment variants, advantages and further features mentioned in the process should equally be applied also to the other claims categories, in particular to the computer program product, to the system and to the connectivity analyzer. In this case the respective functions are realized by way of specific hardware modules which can be provided in a microcontroller or in a (digital or analog) circuit and which perform the respective function.

A further achievement of an embodiment of resides in a connectivity analyzer. By this is to be understood a computer-based or -implemented arrangement for determining available communication functionalities during the configuration or installation of at least one DICOM node in a DICOM network. The connectivity analyzer can be connected as a separate module to the DICOM network via a corresponding interface. Alternatively the connectivity analyzer can already be part of the DICOM network and for example be assigned to a specific DICOM node. In an alternative embodiment variant of the invention the connectivity analyzer is provided on every DICOM node. This has the advantage that connectivity results can be verified by multiple determination.

A further solution according to at least one embodiment of the invention relates to a DICOM network system for determining available communication functionalities in a DICOM network, comprising:
  a multiplicity of DICOM nodes,
  at least one DICOM node requiring to be configured, and
  at least one connectivity analyzer, the DICOM nodes, the DICOM node to be configured and the connectivity analyzer engaging in data interchange via the DICOM network.

A further achievement of at least one embodiment relates to a computer program product. The product is either one which can be loaded directly into a memory of a digital computer and comprises sections of software code with which the steps of the aforementioned method are performed when the computer program product is executed or loaded on the computer. Also understood by the product are storage media (such as e.g. a CD or other portable data medium) on which is stored a computer program which executes the above-described method. In addition the product can consist in computer-implemented modules which are provided on a server for downloading, the modules being designed for performing the above-described method.

An alternative achievement of at least one embodiment the provides a computer program comprising program commands for performing the method described in more detail above. The computer program can be stored as executable code or as object code or source code or in some other form on a digital storage medium.

BRIEF DESCRIPTION OF THE DRAWINGS

Example embodiments of the present invention are described below with reference to the figures, in which:

FIG. 2 is a flowchart of an inventive method according to an example embodiment variant of the invention.

DETAILED DESCRIPTION OF THE EXAMPLE EMBODIMENTS

Figure 1:
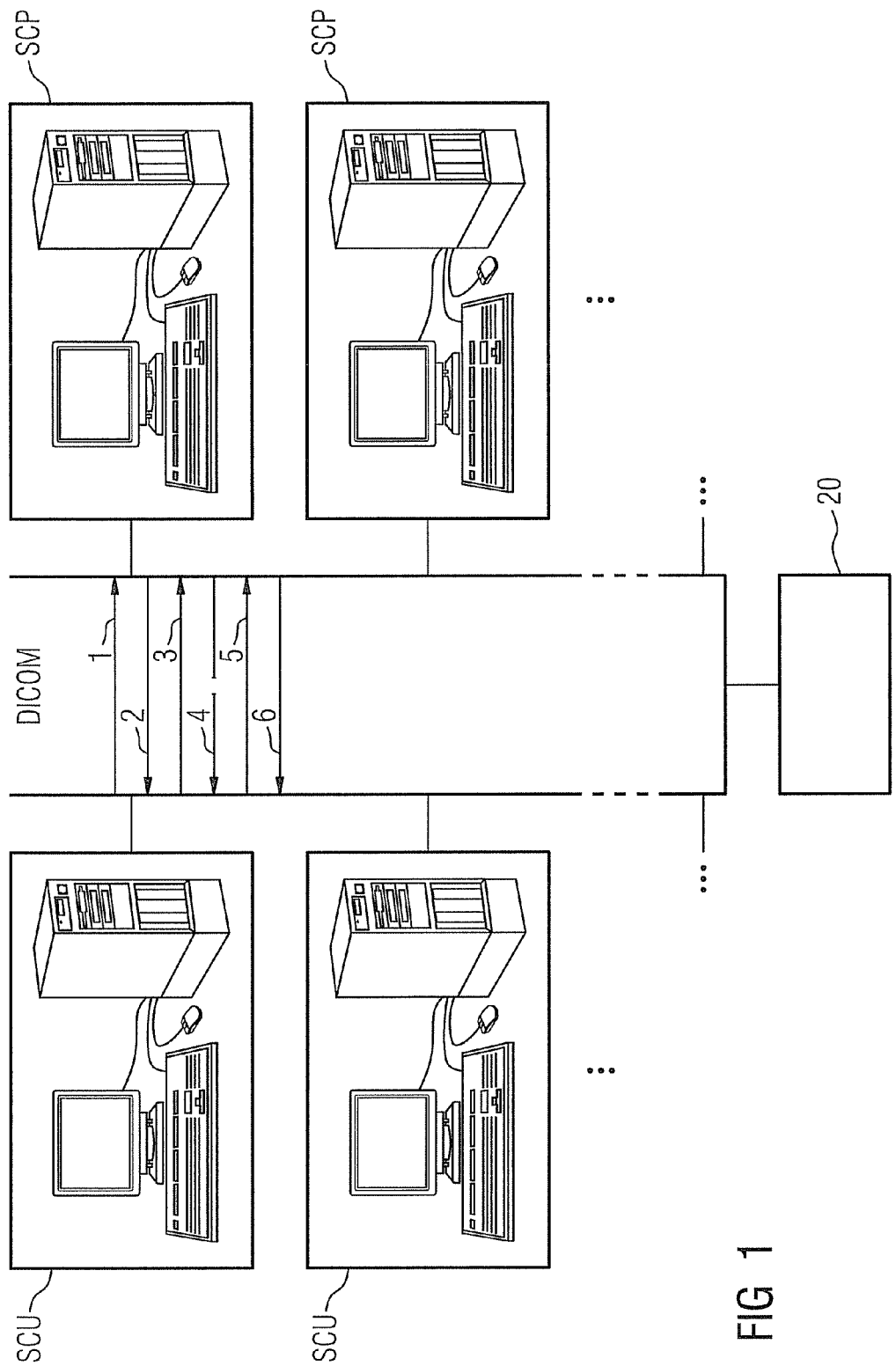
FIG. 1 shows a schematic, overview-like representation of a DICOM network with a connectivity analyzer.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

An embodiment of the invention is explained in more detail below with reference to FIG. 1.

FIG. 1 shows a schematic representation of a DICOM network in the form of an overview.

The DICOM network includes of a multiplicity of DICOM nodes which can act either as Service Class Provider SCP or Service Class User SCU. In the following description a Service Class User is also referred to as an SCU for short and a Service Class Provider also as an SCP for short. The DICOM nodes are computers or computer-based instances which perform radiological functions and are based on digital data processing, such as for example image acquisition devices or the like. All the connected DICOM nodes communicate via a DICOM interface or over the DICOM network. For details relating to the DICOM standard the reader is referred to the publicly accessible documents, in particular the ACR-NEMA DICOM Standards Committee (publisher is the National Electrical Manufacturers Association; published in: Rosslyn, Va., USA 2008), the disclosure content of which should be incorporated into the patent application.

According to an embodiment of the invention a connectivity analyzer 20 is provided (also referred to in the following as a DICOM Network Connectivity Analyzer (DNCA)).

The connectivity analyzer 20 can be connected as a separate product, in particular a computer product (e.g. in the form of a plug-in module which is connected at a slot to the DICOM network via an (e.g. USB) interface), or it can be assigned to an individual DICOM node. Alternatively it can also be provided as a central network instance. It also lies within the scope of an embodiment of the invention to attach the connectivity analyzer 20 as an embedded system to the DICOM network as an electronic module (e.g. a box having corresponding interfaces).

The connectivity analyzer 20 is used to check connectivity parameters for a DICOM node that is to be configured. In particular it is intended to determine available communication functionalities between the DICOM node to be configured and the participating communication partners in the DICOM network. Advantageously this takes place fully automatically.

According to the DICOM standard a device configuration is provided for each new DICOM node to be integrated (a medical or information technology device for example).

Before the respective device can be put into operation it must first be configured. The configuration provides for example that the applications implemented on the DICOM node (application entities, or AEs for short) which are configured on the DICOM device require a specific network connection. Said network connection must be configured. In addition each application makes a list of services or functions (transfer capabilities) available. Examples of DICOM services are:
storage
storage commitment
query/retrieve
basic print
modality work list
modality performed procedure steps
etc.

Most applications require a DICOM node (in the role of SCU) to communicate with another DICOM node (in the role of SCP). It is of course also possible to provide applications in which parallel communication with a plurality of DICOM nodes may be necessary.

The application can only be executed successfully if a connection can be successfully established between SCU and SCP.

According to an embodiment of the invention it is thus provided that testing of required communication functionalities between the participating DICOM nodes is carried out already in the configuration phase that precedes the actual operating phase. The purpose of this is to verify whether the necessary DICOM communications can also take place between the participating nodes.

According to an embodiment of the invention the DICOM protocol is used for that purpose for the communication.

Communication connections according to the DICOM standard are always set up in the same way. The DICOM node in the role of the SCU submits a connection request (communication request) to the partner DICOM node (in the role of the SCP). In this request it is communicated which type of connection is desired. In other words the communication parameters are also sent at the same time here. The transfer syntaxes supported by the SCU are also transmitted. This means that along with the communication request 1, 3, 5, . . . is sent how the numbers are encoded, whether a so-called value representation is specified explicitly, and whether the images are packed. Further connection parameters can also be sent in addition. The so-called SOP (Service Object Pair) classes supported by the SCU are also transferred. For each SOP class, information is transmitted indicating whether it is supported as SCU or as SCP.

In reply to the communication request 1, 3, 5, . . . the SCP sends back a communication response 2, 4, 6. The communication response 2, 4, 6 comprises the supported presentation contexts. At the same time the application entities (AEs) are also transferred so that the SCP can decide whether a communication is possible with this application name.

Following the connection setup the actual DICOM communication can take place. In this case it is provided that for all the communication connections a response will be made to every request, indicating whether the request could be answered successfully or not.

According to an embodiment of the invention it is thus provided that trial or test communication requests will be sent from the SCU to the SCP and corresponding trial or test responses communicated already at installation or configuration time. In FIG. 1 the test requests are labeled with the reference numerals 1, 3 and 5, and the test responses to said requests with the reference numerals 2, 4 and 6. According to the invention the connectivity analyzer 20 is embodied to generate said test requests 1, 3, 5 and to receive the respective test responses 2, 4, 6 of the SCP.

Advantageously the received responses are analyzed and examined to determine whether the request was able to be successfully answered (or executed on the SCP). If this is possible, the respective communication functionality is flagged as "available" in the SCU. Otherwise (i.e. if it was not possible to respond successfully to the test communication request 1, 3, 5) an error message is generated. In that case the respective communication functionality is represented as "not available" in the SCU.

After all the test communication responses 2, 4, 6 have been received in the SCU, the corresponding communication functionality can be flagged as "available" or "not available". The interrupted arrow of the communication response 4 in FIG. 1 is intended to indicate that the communication request 3 could not be successfully executed. In this case the respective communication functionality of the application is flagged at the SCU as not supported. All the other communication requests 1 and 5 in FIG. 1 are available, because they could be successfully executed on the SCPs.

Thus, already at the configuration phase the technician can receive information indicating whether the respective communication functionalities required by the applications are in fact available. In particular it is investigated whether the communication functionalities are available on the remote communication partners (there may also be a plurality thereof) that assume the role of the SCP.

In an embodiment of the invention, provision is made for an extension function to be provided if the requisite communication functionalities are not available. In that case it is investigated whether the requisite add-on functionality that is missing on the remote SCP node can be provided on the SCU node (or on other network nodes) and compensate for the missing functionality. If this is possible, a corresponding communication request is sent to the replacement node and if this can be answered with a successful response the communication functionality can be flagged as available (on the SCU).

The execution sequence of the method according to a preferred embodiment variant is described below with reference to FIG. 2.

As can be seen in FIG. 2, the commissioning sequence for a new DICOM device is typically divided into a configuration phase and an operating phase (designated as Runtime in FIG. 2). The configuration phase serves for installation of the device and the operating phase relates to the implementation of the configured DICOM node and hence to the runtime of the applications that are installed on the DICOM node or, as the case may be, to the realization of the respective services and functions.

In a first step 100 an order requesting configuration (or installation) of a DICOM node is registered.

In step 110 the node for which the configuration is to be performed is integrated (provisionally) into the DICOM network.

Next, in step 120, it is registered which applications are installed on the node that is to be configured.

In step 130 it is registered which communication functionalities are required by the applications and hence by the node. The connectivity parameters for the communication functionalities are registered at the same time.

In step 140 a (test) communication request is generated. This is sent by the SCU to the SCP (as communication partner). The actual communication request is therefore executed in step 140.

Steps 100 to 140 inclusive are usually performed on the connectivity analyzer 20.

In reply to the communication request a response to the respective communication request 1, 3, 5 is then generated on the SCP. The response to the communication requests (this is labeled with the reference numeral 2, 4 and 6 in FIG. 1) is thereupon sent from the SCP to the SCU.

Next, in step 160, the result of the communication request or the communication response 2, 4 and 6 can be received on the SCU.

In step 170 the result of the communication request 2, 4, 6 is analyzed. It is analyzed in particular here whether it was possible to respond successfully to the connection or not.

Next, in step 180, the respective node can be configured on the basis of the result.

Steps 170 and 180 are likewise usually performed on the connectivity analyzer 20.

In step 190 the configured node can then be put into operation (Runtime). At the same time the communication functionalities are adapted to match the respective communication partners of the node.

The dots in FIG. 2 below step 190 are intended to indicate that it is also possible to perform further adaptation steps at runtime.

Furthermore the arrow pointing downward in a functional sense and leading upward in a loop in FIG. 2 is intended to indicate that according to the invention not only are new configurations possible, but that a repeated or modified configuration is also possible even after a node has been put into operation. This can be useful for example if the processing conditions have changed (for example if further communication partners have joined or further applications have been added to the respective nodes).

The important point is that the settings of the respective node are completed during the configuration phase, i.e. the address, ports, services and further functionalities are defined for example. In this case it should be noted that said settings and configurations are manufacturer- and model-dependent. Advantageously, the tool according to at least one embodiment of the invention enables all available communication functionalities to be provided already in the configuration phase, and moreover independently of the respective manufacturer and the respective model of the DICOM node. In other words all the available communication functionalities can be provided in a manufacturer- and model-neutral manner by way of a targeted method. In every case the functionalities are provided automatically, rendering it unnecessary to analyze the conformance statement (either manually or automatically).

It should once again be highlighted as an advantage that the approach according to the invention can also be used for reconfiguring already configured DICOM nodes. This is useful for example if new inventory nodes make further functionalities available or further devices are attached to the DICOM network.

Returning once more to the flow sequence depicted in FIG. 2, it should be emphasized that there are basically two possibilities for generating the test communication requests 1, 2, 3, 5. On the one hand it is possible to execute these sequentially, i.e. after a first communication request 1 the respective communication response 2 is always waited for and evaluated. Then the next communication request 3 and its response 4 are processed in a next step. On the other hand it is possible to depart from this sequential procedure and already generate all or selected test communication requests 1, 2, 3, 5, . . . and send them to the different communication partners SCP in parallel in order thereafter to process their responses 2, 4, 6.

The further nodes SCU, SCP shown in FIG. 1 are intended to indicate that a multiplicity of DICOM nodes can belong to the DICOM network and their interoperability can be verified by way of the tool according to an embodiment of the invention.

The result of the connectivity analyzer 20 is stored and can be reused for the further operating phase or for further configuration processes or, as the case may be, for adapting the existing DICOM network.

Because DICOM communication is based on a client-server model, the inventive method can also be implemented according to the client-server principle. In this case individual method steps can also be performed on different computer-based instances and, as it were, in a distributed system. Thus, in particular the available communication functionality can be registered on a different computer-based instance from that on which the registered communication functionality is provided. Typically, the communication functionality is registered automatically on the connectivity analyzer 20 and the registered communication functionality is provided on the respective SCU or on the user interface of the SCU.

According to one aspect, at least one embodiment of the present invention is embodied onto a computer-implemented method for determining available communication functionalities during the configuration of at least one DICOM device (or DICOM node) in a DICOM network, wherein the method comprises:

automatically registering the available communication functionality of the DICOM node;

providing the registered communication functionality for the purpose of configuring the DICOM node prior to its entry into operation with a communication request.

The concepts used within the scope of the present patent application shall be explained in more detail below.

The method of one embodiment is a computer-implemented method which can be used as an automatic tool for configuring DICOM devices for integration into a DICOM network. If the (new) DICOM device that is to be configured is intended to interact for example with one or more other (old) DICOM devices, the connectivity between the new and the first old DICOM device, as well as between the new and the second old DICOM device can be analyzed in advance. The analysis can also be performed for a remote DICOM node so that it can be ascertained on an already integrated (old) DICOM node which communication functionalities are provided by the new (soon to be integrated) DICOM node.

Communication functionalities are determined by way of the tool according to an embodiment of the invention. This basically relates to (all or selected) relevant parameters for configuring a DICOM device. With the DICOM standard (in particular Version 3.0) all manufacturers are mandated to collate and provide all DICOM-relevant characteristics of the device in so-called SOP (Service Object Pair) classes. For message exchange purposes the DICOM standard defines a message transfer service, specifically a DICOM Message Service Element (DIMSE), which is based on a TCP/IP, ISO-OSI or point-to-point interface. The combination of an information object and a service is referred to in the DICOM standard—as already mentioned above—as a Service Object Pair (SOP).

During the actual connection setup SOP classes which are supported by both communication partners (or applications) are determined initially. In addition providers and users of the respective service are determined. The communication functionality in each case comprises communication parameters, such as for example the services provided by the respective DICOM node, the SOP-class-supported transfer syntaxes, as well as further communication parameters, such as for example the maximum PDU size (PDU: Protocol Data Unit), extended negotiations as extended services between two applications, a presentation context, parameters for asynchronous windowing, parameters which define whether for example a value representation is specified explicitly or implicitly, how integer numbers are encoded (little-endian or big-endian format), how images are packed or not, how these are encoded, etc. Further configuration parameters can also be added here depending on how the participating DICOM device is used, so the list can be configured dynamically according to the application.

Depending on how many DICOM devices are engaged in exchanging data with one another, all the communication functionalities on the participating devices are checked and registered according to the invention. If, however, it is merely intended to integrate a new DICOM node into an existing network, it is possible to provide the communication functionalities of the remote DICOM node that is to be newly integrated, on an existing DICOM node.

The term "DICOM node" refers to all DICOM-compatible modules, devices and products that are normally provided by different manufacturers. A DICOM node can be a device (for example for displaying image data, for storing image data, for post-processing digital image data, for acquisition of the image data, etc.). One or more applications (so-called Application Entities (AEs)) can run on the DICOM node.

According to the DICOM standard a DICOM node can assume the role of a Service Class Provider (SCP) or the role of a Service Class User (SCU). The Service Class Provider makes a particular service available, while the Service Class User uses the service. In principle it is possible for a node to assume both roles (SCU and SCP) simultaneously.

The term "DICOM network" is intended to denote a network consisting of DICOM nodes and DICOM-compatible nodes. According to one embodiment variant it is also possible for DICOM-external devices to be integrated into the DICOM network. Usually the devices which are not DICOM-compliant are integrated into the network via a separate interface (adapter module).

The term "configuration" of the DICOM node refers to a time phase that lies prior to the commissioning or entry into operation of the respective DICOM node. Thus, before the respective DICOM node is integrated into the DICOM network and hence before an actual connection can be negotiated, the respective node must first be configured. According to an aspect of an embodiment of the invention, the communication functionalities can be provided already at the time of the configuration and therefore before a connection negotiation can take place between the respective DICOM nodes. The provided communication functionalities are used for configuring the DICOM node.

The communication functionality of the participating DICOM nodes is no longer registered manually through analysis of the conformance statement, but fully automatically and in particular without user interaction.

The registered communication functionalities are provided already in the configuration phase and can therefore be used in order to align the communication of the participating DICOM nodes to one another. Providing can include displaying and further processing. The displaying function is usually realized on a graphical user interface of a monitor.

An important aspect and advantage of an embodiment of the invention is to be seen in knowing the behavior of a remote DICOM node already at a preliminary stage, in particular in a configuration phase for the DICOM node. As a result a message can be output already at configuration time if the respective communication functionalities of the participating DICOM nodes are not compatible and a connectivity problem is to be expected. Furthermore it becomes possible for a Service Class User (SCU) to present only those applications or application cases or services that are also supported by the remote DICOM node.

According to an advantageous development of an embodiment of the invention it is provided to further process the registered and provided communication functionalities. The further processing provides that in the absence of a concordance (between SCU and SCP for example) a request is made for an automatic functionality extension, in particular on the SCP node. If possible this extended functionality can also be provided by the SCU node.

An important aspect of an embodiment of the present invention is to be seen in the fact that the available communication functionality or functionalities is or are already provided in a configuration phase. The "configuration phase" refers to the hardware-related connection or integration of the at least one DICOM node into the DICOM network.

The configuration phase therefore relates to an installation process for the respective DICOM device. On a timeline the configuration phase comes before an operating phase. The "operating phase"/(runtime) of the DICOM node refers to the time period in which the respective DICOM node is put into operation in the DICOM network, i.e. to the runtime of the DICOM node during which the services and functions of the DICOM node are performed. Previously these two phases (configuration phase and operating phase) were completely separate from each other.

According to an embodiment of the invention it is now provided to interleave the two phases so that a pilot operating phase is already implemented in the configuration phase, the pilot operating phase being embodied to analyze the available communication functionalities of the participating DICOM nodes. The pilot operating phase differs from the (actual) operating phase in that the communication operation of the participating DICOM nodes is performed as it were only by way of a test and without an actual communication order from an application (communication request, association request, association response). The pilot operating phase serves simply to send test communication requests to the respective DICOM node and to receive and analyze its corresponding responses thereto. If the test or trial request signals with the respective response that the trial order can be successfully executed, this is stored as an available communication functionality of the DICOM node. Otherwise (i.e. if the trial request could not be performed successfully) the functionality is characterized as not available.

As already mentioned, it is provided according to one aspect of an embodiment of the present invention that the registered communication functionality or functionalities is or are provided already at the time of installation of the DICOM node. This has the advantage that only those services and functions of the nodes are presented on a user interface that will actually be able to be performed without connectivity problems. Moreover the actual connection negotiation in the operating phase of the DICOM network can be made shorter and more efficient, since relevant connectivity parameters have already been registered and provided.

Embodiments of the invention is categorically not limited to a specific number of DICOM nodes that are to be integrated. Only a new or newly to be configured DICOM node for which the available communication functionalities are to be registered and provided can therefore be scheduled to be integrated into a network. Equally it is possible that a plurality of DICOM nodes for which the respective communication functionalities are to be determined are intended to be integrated into the network simultaneously or sequentially.

As already mentioned above, it is possible for one DICOM node to comprise a plurality of applications. Generally an application has different communication requirements. In such a scenario it is provided that all the relevant communication functionalities are automatically registered, tested and determined for all applications of the DICOM node.

In a preferred development of an embodiment of the invention, it is provided that the communication functionalities requested by the SCU and the communication functionalities provided by the SCP are compared. If the comparison identifies a concordance, an availability message can (optionally) be output. Furthermore the application required by the respective communication functionality can be flagged as executable on the SCU.

In the event of an incorrect match, i.e. if the requested communication functionality cannot be provided on the SCP, an error message can be generated. In addition or alternatively the respective application can be flagged on the SCU that requested the communication functionality as not available (or as not activatable or not supported) on the monitor interface.

In a development it can be provided that in the event of an error, i.e. if the requested communication functionality cannot be provided on the SCP, an extension module will be provided which is embodied to provide the requested communication functionality as an add-on communication functionality. For example, the add-on functionality can be provided on the SCU for the remote SCP. In this embodiment variant the approach is therefore similar to the approach that is known from cloud computing. With the latter approach, functions and services are provided, not locally, but by remote network nodes.

One result of the method according to an embodiment of the invention relates to the provisioning of the registered communication functionalities. In an alternative embodiment variant the result alternatively or additionally includes also a classification of the SCU applications. In this case the classification is carried out according to the criteria "Is supported in respect of the communication functionality" and "Is not supported in respect of the communication functionalities". The result is stored. In particular the result is stored locally for a remote DICOM node. At runtime, i.e. during the operating phase, all applications access the local memory and consequently can access the result of the connectivity analysis at runtime and at the same time adapt the behavior of the application to the current connectivity results, which in turn improves the runtime behavior and makes the connection negotiation faster.

It can be retained as an important advantage of the method according to the invention that an automatic analysis of communication functionalities is possible by means of the tool. Furthermore said analysis can also be carried out for a remote system, using conventional communication protocols and calibration possibilities. In other words no additional, special-purpose protocol needs to be used.

Furthermore the data transmission can be simplified and speeded up by, for example, adapting conversion processes (for example compression/decompression) used during the data transmission already at the preliminary stage to the transfer syntax supported in the particular case, before the connection channel has been opened.

Furthermore the "Image Send" functionality can for example be adapted such that the list of (remote) receiver nodes is adapted to the respective SOP class of the respective image so that as a result only those receiver nodes are represented as selectable which possess the necessary communication functionality for receiving the image.

In addition specific DICOM network nodes can be singled out for archiving and prefetching tasks as a function of storage requirements (storage commitment, query/retrieve).

A further advantage is to be seen in the fact that special connectivity parameters can be registered which are relevant to the respective application (to the respective node). This enables the determination of the available communication functionalities to be specifically tailored to the respective application case. This was not possible in the prior art, since the conformance statements were converted manually in each case. If the respective connectivity parameter was not included in the conformance statement, no definitive information about the connectivity parameters could be derived. According to an embodiment of the invention, this is now different, since all connectivity parameters can be analyzed in accordance with the requirements profile.

A further achievement of an embodiment of resides in a connectivity analyzer. By this is to be understood a computer-based or -implemented arrangement for determining available communication functionalities during the configuration or installation of at least one DICOM node in a DICOM network. The connectivity analyzer can be connected as a separate module to the DICOM network via a corresponding interface. Alternatively the connectivity analyzer can already be part of the DICOM network and for example be assigned to a specific DICOM node. In an alternative embodiment variant of the invention the connectivity analyzer is provided on every DICOM node. This has the advantage that connectivity results can be verified by multiple determination.

The connectivity analyzer of at least one embodiment comprises:

at least one detection module which is intended for automatically registering the available communication functionality of the respective DICOM node, and at least one provider module which is intended for automatically providing the detected communication functionality or functionalities of the respective DICOM node.

In this case it is provided that the provider module provides the detected communication functionalities in the configuration or installation phase of the respective DICOM node and consequently already prior to entry into operation with an actual communication request of the respective DICOM node.

Advantageously the actual communication request of the respective application of the DICOM node can then be specifically adapted to match the available connectivity parameters.

The connectivity analyzer can be developed with the features that have been described hereintofore in connection with the method.

A further solution according to at least one embodiment of the invention relates to a DICOM network system for determining available communication functionalities in a DICOM network, comprising:

a multiplicity of DICOM nodes, at least one DICOM node requiring to be configured, and at least one connectivity analyzer, the DICOM nodes, the DICOM node to be configured and the connectivity analyzer engaging in data interchange via the DICOM network.

A further achievement of at least one embodiment relates to a computer program product. The product is either one which can be loaded directly into a memory of a digital computer and comprises means or sections of software code with which the steps of the aforementioned method are performed when the computer program product is executed or loaded on the computer. Also understood by the product are storage media (such as e.g. a CD or other portable data medium) on which is stored a computer program which executes the above-described method. In addition the product can consist in computer-implemented modules which are provided on a server for downloading, the modules being designed for performing the above-described method.

An alternative achievement of at least one embodiment the provides a computer program comprising program commands for performing the method described in more detail above. The computer program can be stored as executable code or as object code or source code or in some other form on a digital storage medium.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE SIGNS

DICOM DICOM network
SCU Service Class User
SCP Service Class Provider
20 Connectivity analyzer/DICOM Connectivity Analyzer—DNCA
1, 3, 5 . . . (Test) communication request
2, 4, 6, . . . (Test) communication response
100 Register configuration order for a DICOM node
110 Integrate nodes to be configured into network
120 Register applications on the nodes to be configured
130 Register communication functionalities required for the applications
140 Automatically generate a test communication request
150 Execute the test communication request
160 Receive test result as response to the test communication request
170 Process test result of the communication response 2, 4, 6,

180 Configure the node on the basis of the result
190 Commission the configured node

What is claimed is:

1. A method for determining available communication functionalities during the configuration of at least one DICOM device in a DICOM network, comprising:
    automatically registering the available communication functionality of the at least one DICOM device; and
    providing the registered communication functionality for the purpose of configuring the DICOM device prior to a communication request of the at least one DICOM device,
    determining all of the communication functionalities required for an application, wherein,
        the determined required communication functionalities are compared with the registered available communication functionalities and wherein an error message is generated automatically in the event of non-conformance and in the event of non-conformance, an add-on communication functionality is provided, the add-on communication functionality being provided on a Service Class User for a remote Service Class Provider.

2. The method as claimed in claim 1, wherein the registered communication functionality is provided automatically and already in a configuration phase for the DICOM device and consequently prior to its entry into operation with actual connection negotiations.

3. The method as claimed in claim 2, wherein at least one of one DICOM device acts as Service Class Provider and one DICOM device acts as Service Class User.

4. The method as claimed in claim 2, wherein communication functionalities are determined for a plurality of DICOM devices.

5. The method as claimed in claim 1, wherein at least one of one DICOM device acts as Service Class Provider and one DICOM device acts as Service Class User.

6. The method as claimed in claim 1, wherein communication functionalities are determined for a plurality of DICOM devices.

7. The method as claimed in claim 1, wherein unavailable communication functionalities are represented on a user interface of a Service Class User as not supported, while available communication functionalities are represented as supported.

8. The method as claimed in claim 1, wherein the available communication functionalities for a remote DICOM device are registered using the DICOM protocol.

9. A non-transitory computer readable medium including program segments for, when executed on a computer device, causing the computer device to implement the method of claim 1.

* * * * *